(12) United States Patent
Burns et al.

(10) Patent No.: US 8,658,091 B2
(45) Date of Patent: Feb. 25, 2014

(54) USING SUPERCRITICAL CARBON DIOXIDE TO REMOVE RESIDUAL ETO FROM SUTURES

(75) Inventors: David Burns, Ithaca, NY (US); Anastasia J Nichols, Ithaca, NY (US)

(73) Assignee: Novasterilis, Inc., Lansing, NY (US)

( * ) Notice: Subject to any disclaimer, the term of this patent is extended or adjusted under 35 U.S.C. 154(b) by 255 days.

(21) Appl. No.: 13/233,839

(22) Filed: Sep. 15, 2011

(65) Prior Publication Data

US 2013/0072970 A1  Mar. 21, 2013

(51) Int. Cl.
*A61L 2/20* (2006.01)
*A61L 2/00* (2006.01)
*A61L 2/18* (2006.01)
*A61L 9/00* (2006.01)

(52) U.S. Cl.
USPC ............... 422/33; 422/28; 422/30; 422/34

(58) Field of Classification Search
USPC .......................................... 422/33, 34, 28, 30
See application file for complete search history.

(56) References Cited

U.S. PATENT DOCUMENTS 6,149,864 A * 11/2000 Dillow et al. ............... 422/28
6,440,364 B1    8/2002 Vera et al.

FOREIGN PATENT DOCUMENTS

EP        1040840 A1 * 10/2000 ................ A61L 2/20

* cited by examiner

*Primary Examiner* — Regina M Yoo
(74) *Attorney, Agent, or Firm* — Welsh Flaxman & Gitler LLC

(57) ABSTRACT

Treating absorbable sutures that have been sterilized using ethylene oxide with carbon dioxide at or near its supercritical pressure and temperature conditions to remove any residual ethylene oxide.

12 Claims, 2 Drawing Sheets

USING SUPERCRITICAL CARBON DIOXIDE TO REMOVE RESIDUAL ETO FROM SUTURES

BACKGROUND OF THE INVENTION

1. Field of the Invention

The present invention relates to using carbon dioxide, at or near its supercritical pressure and temperature conditions, to remove residual ethylene oxide (EtO) from absorbable surgical sutures. EtO, although an effective sterilant, is a carcinogenic and mutagenic chemical with direct impact on wound healing.

2. Description of the Related Art

It is common to sterilize absorbable surgical sutures using ethylene oxide as set forth in U.S. Pat. No. 6,440,364. However, the process disclosed in the '364 patent has been found to leave residual ethylene oxide on the sutures. This residual ethylene oxide has been found to cause irritation suture induced inflammation when used in some patients. It has also been found that ethylene oxide is carcinogenic. Still further, it has been found the residual ethylene oxide compromises mechanical properties of the suture. Therefore, it would be desirable to remove all ethylene oxide after sterilization. It is towards fulfilling such a need that the present invention is directed.

SUMMARY OF THE INVENTION

The method of the present invention is directed to treating absorbable sutures, after they are sterilized using ethylene oxide, with supercritical carbon dioxide to remove all residual ethylene oxide. In accordance with a preferred embodiment, absorbable sutures in a gas permeable package are placed in a basket which is inserted into a reactor vessel. Carbon dioxide is then introduced into the reactor vessel while being pressurized and heated to supercritical levels above 1099 psi and 31.1 C. The sutures, depending upon the number, are allowed to sit in the pressurized and heated reactor vessel from 1 second to 4 hours while the supercritical fluid is stirred, preferably 30 to 60 minutes. Upon completion of the specified time, the reactor vessel is depressurized. Depressurization times can range from 15 seconds to 30 minutes. The basket containing the packaged sutures is removed and the sutures are ready for shipping or repackaged for shipping.

Other objects and advantages of the present invention will become apparent from the following detailed description when viewed in conjunction with the accompanying drawings, which set forth certain embodiments of the invention.

DESCRIPTION OF THE PREFERRED EMBODIMENT

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as a basis for teaching one skilled in the art how to make and/or use the invention.

Figure 1:
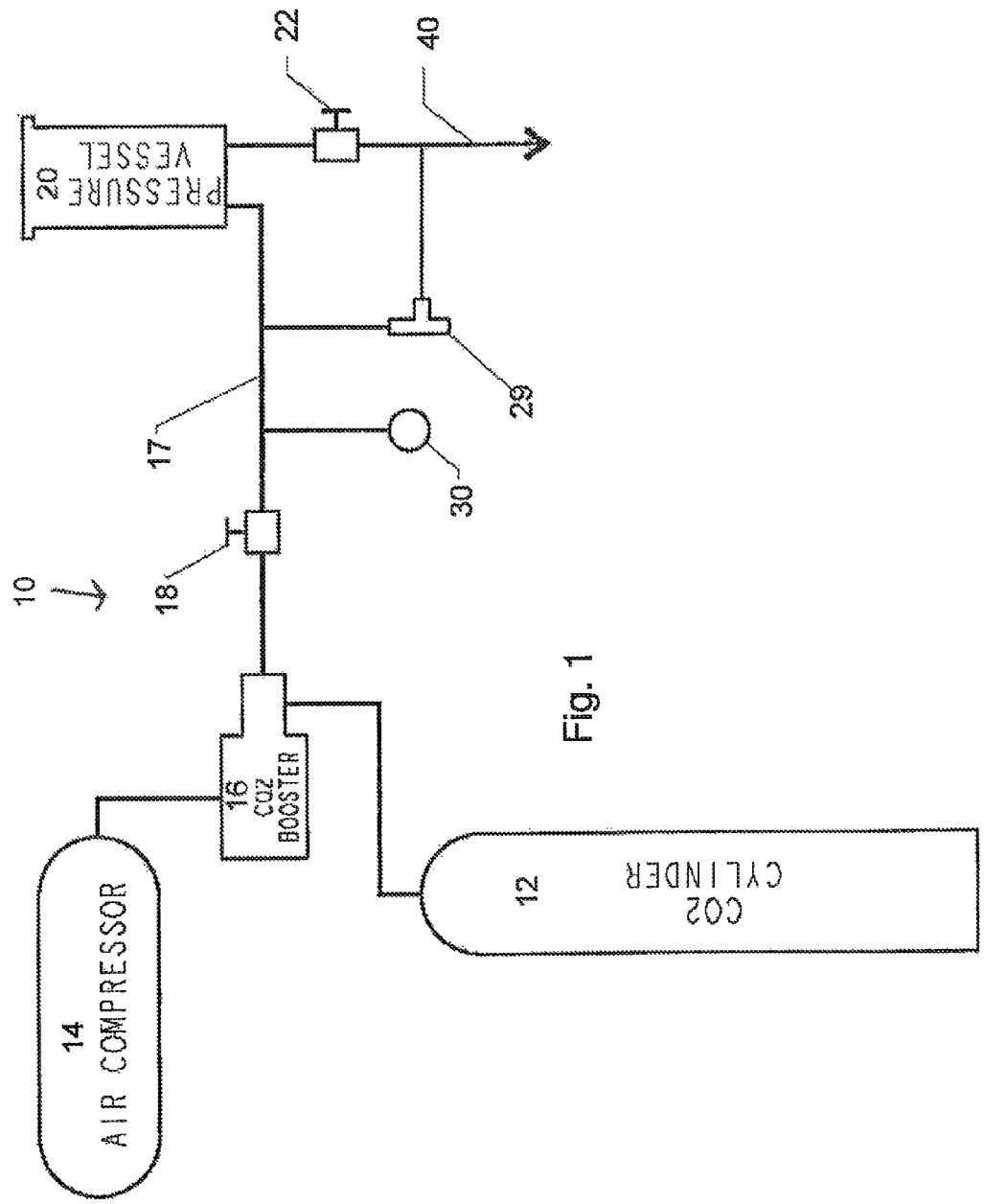
FIG. 1 is a schematic view of a preferred apparatus used for treatment.
Figure 3:
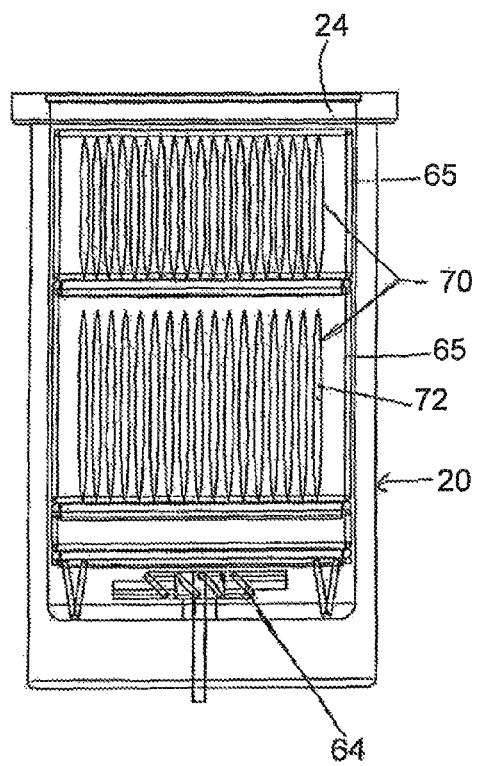
FIG. 3 shows the reactor vessel open with packaged sutures in baskets placed into the reactor vessel.
Figure 2:
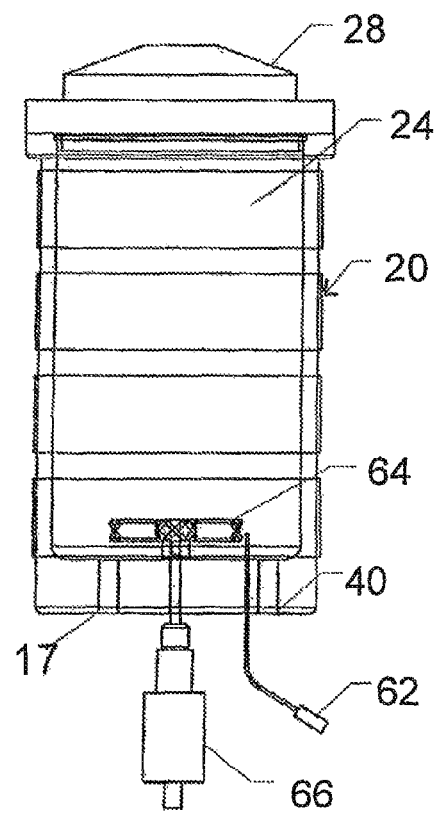
FIG. 2 is a detailed schematic view of the reactor vessel employed in the apparatus of FIG. 1.
Figure 4:
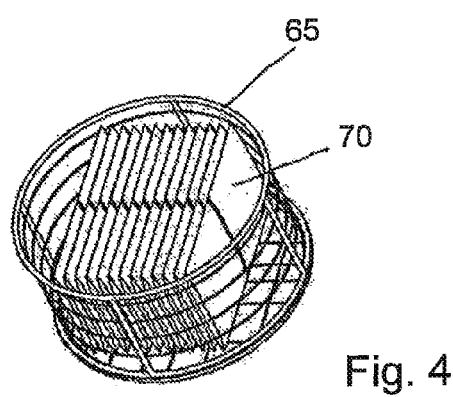
FIG. 4 shows a basket containing treated sutures in a plurality of packages.

With reference to FIG. 1, an apparatus according to the present invention is depicted. The apparatus 10 includes a standard compressed gas cylinder 12 containing carbon dioxide, and a standard air compressor 14 used in operative association with a carbon dioxide booster 16 (e.g., Haskel Booster ALG-32). Alternatively, it is appreciated the air compressor and booster can be replaced with a single carbon dioxide compressor.

The carbon dioxide is introduced to a reactor vessel 20 from supply line 17 via valve 18. A pressure gauge 30 is provided in supply line 17 to allow the pressure to be monitored. In order to prevent an overpressure condition existing in line 17, a pressure relief valve 29 may be provided. An outlet line 40 through valve 22 allows the reactor vessel 20 to be depressurized.

The reactor vessel 20 is most preferably constructed of stainless steel (e.g., 316 stainless steel) and has a total internal volume sufficient to accommodate the materials being treated either on a laboratory or commercial scale. For example, in laboratory studies, an internal volume of 20 L (e.g., approximately 22 inches long by about 10 inches inside diameter) was deemed adequate. The reactor vessel 20 includes a temperature control unit 62 and a mechanical stirring system most preferably comprised of an impeller 64 and a magnetic driver 66. The reactor vessel 20 contains a conventional basket 65 which is also preferably constructed of stainless steel. The basket 65 serves to hold the sutures 72 to be treated as well as to direct the carbon dioxide in a predetermined manner. The top 28 of the reactor vessel 20 may be removed when depressurized to allow access to the reactor vessel's interior 24.

In use, the sutures 72 to be treated are placed in basket 65 while still in their commercial gas permeable pouch or "as sold" packaging 70 and introduced into the interior space 24 of the reactor vessel 20. The "as sold" packaging is the packaging in which the sutures are originally packaged when treated with ethylene oxide and intended for commercial sale. The temperature control unit 62 is operated so as to set the desired initial temperature between 31.1 and 45 C for treatment. The reactor vessel 20 may then be pre-equilibrated with carbon dioxide from gas cylinder 12 at atmospheric pressure. Thereafter, the magnetic driver 66 is operated so as to activate the impeller 64. The reactor vessel 20 may then be pressurized to a desired pressure of greater than 1099 psi by introducing additional carbon dioxide gas from cylinder 12 via the air compressor 14 linked to booster 16. The reactor vessel 20 is pressurized and heated to supercritical levels above 1099 psi and 31.1 C. The sutures are allowed to sit in the pressurized and heated chamber for 1 second to 4 hours while the supercritical fluid is being stirred. Optimally, a time period between 30 to 60 minutes has been found to be effective in removing all residuals of EtO, though treating for more than 60 minutes may be required depending upon the number of sutures and amount of residual EtO needing to be removed. Upon completion of the desired time period, an outlet line 40 controlled by a valve 22 allows the reactor vessel to be depressurized. Depressurization times can range from 15 seconds to 30 minutes.

Results show an untreated control suture has a cytotoxicity score of a 2 or 3 (out of 4). A suture treated in accordance with the present invention has a score of 0, indicating removal of all residual EtO. Scores are obtained through an established ISO standard protocol where c2c12 mouse cells are exposed to the suture extract. A score of zero means all or most of the cells did not die from the direct exposure. A score of 2 means the exposure had to be diluted twice for the cells to survive. Cytotoxicity is a major side effect in today's absorbable sutures. Although EtO has currently acceptable levels of residual gas from 1 to 10+ ppm, optimally the complete removal or absence of chemical residuals would be preferable. Sutures, as well as other medical items, are allowed residuals, because it's the only current acceptable way to sterilize half or most of medical products in the world. Currently in the U.S. 10 ppm EtO residuals in steroidal drugs is acceptable, whereas in the EU and accordance with the Kyoto Treaty only 1 ppm of residuals is acceptable.

While the preferred embodiment has been shown and described, it will be understood that there is no intent to limit the invention by such disclosure, but rather, is intended to cover all modifications and alternate constructions falling within the spirit and scope of the invention.

The invention claimed is:

1. A method of treating sutures that have been sterilized using ethylene oxide with carbon dioxide at or near its supercritical pressure and temperature conditions to remove any residual ethylene oxide.

2. The method of claim 1, wherein the sutures are absorbable.

3. The method of claim 1, wherein the treating of the sutures occurs while they are placed in a basket in their original gas permeable package intended for commercial sale.

4. The method of claim 1, wherein the treating of the sutures occurs for 30 to 60 minutes.

5. The method of claim 1, wherein the treating of the sutures occurs for more than 60 minutes.

6. The method of claim 1, wherein the sutures are contained within a gas permeable package during treating.

7. A method for treating surgical sutures after they are sterilized using ethylene oxide to remove any residual ethylene oxide comprising:
   placing the surgical sutures into the interior of a reactor vessel;
   introducing carbon dioxide into the reactor vessel while being pressurized and heated to supercritical levels above 1099 psi and 31.1° C.;
   maintaining the surgical sutures in contact with supercritical carbon dioxide for a predetermined period of time;
   depressurizing the reactor vessel; and
   removing the surgical sutures from the reactor vessel.

8. The method of claim 7, wherein the surgical sutures are absorbable.

9. The method of claim 7, wherein the surgical sutures are in their original gas permeable package intended for commercial sale when placed in the reactor vessel.

10. The method of claim 7, wherein the predetermined period of time is 30 to 60 minutes.

11. The method of claim 7, wherein the predetermined period of time is for more than 60 minutes.

12. The method of claim 7, wherein the surgical sutures are contained within a gas permeable package during contact with the supercritical carbon dioxide.

* * * * *